United States Patent [19]

Graudums et al.

[11] 4,067,985

[45] Jan. 10, 1978

[54] LACTUM DRUG COMPOSITIONS

[75] Inventors: Ivars Graudums, Stolberg, Rhineland; Heinrich Mückter, Aachen; Ernst Frankus, Stolberg-Busbach, all of Germany

[73] Assignee: Chemie Grunenthal GmbH, Stolberg, Germany

[21] Appl. No.: 640,288

[22] Filed: Dec. 12, 1975

Related U.S. Application Data

[62] Division of Ser. No. 336,313, Feb. 27, 1973, Pat. No. 3,951,985.

[30] Foreign Application Priority Data

Mar. 3, 1972 Germany .............................. 2210166

[51] Int. Cl.$^2$ ..................., A61K 31/33; A61K 31/40; A61K 31/425; A61K 31/445

[52] U.S. Cl. .................................. 424/267; 424/244; 424/270; 424/274

[58] Field of Search ................................ 424/270, 267

[56] References Cited

U.S. PATENT DOCUMENTS 3,314,960  4/1967  Freed et al. .......................... 260/281

*Primary Examiner*—Stanley J. Friedman
*Attorney, Agent, or Firm*—Weiser, Stapler & Spivak

[57] ABSTRACT

Drug compositions including a lactam of the substituted ortho-sulfobenzoic acid imido pyrrolidone-2, piperidone-2, or caprolactam type.

The drug compositions have valuable therapeutic properties: they are immunosuppressive, sedative and have antitumor activity. The method of inducing sedation in warmblooded animals.

28 Claims, No Drawings

LACTUM DRUG COMPOSITIONS

This is a division, of application Ser. No. 336,313 filed Feb. 27, 1973 now U.S. Pat. No. 3,951,985.

The present invention relates to new lactams which have valuable properties as pharmaceuticals and which may be used as intermediates for the manufacture of pharmaceuticals. Further, the present invention relates to a process for the manufacture of these compounds. The new compounds according to the invention have the general formula

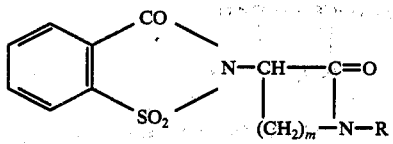

wherein R indicates a hydrogen atom or an alkyl radical with 1 to 3 carbon atoms and $m$ represents a number 2, 3 or 4. Preferably R represents a hydrogen atom and $m$ the number 2 or 3.

Compounds of the general formula I are effective as sedatives and hypnotics in warm blooded mammals like in man and animals. In addition, they suppress the immunological reactions in leprosy and thus may be used as immunosuppressive drugs. Moreover, there is evidence that these compounds inhibit growth of hormone-depending tumors.

Compounds used in treatment of similar disorders and/or of similar chemical structures are known, for instance, 3-phthalimido-piperidinedione-2,6 (Thalidomide); see U.S. Pat. No. 2,830,991) and 3-(o-sulfobenzoic acid imido)piperidinedione-2,6 (see U.S. Pat. 3,314,960). The compounds according to the present invention differ from the other known substances by then higher effectiveness and/or lack of side effects. Though Thalidomide is widely used now in treatment of leprosy, care must be taken in young females because some investigators observed teratogenic effects in animals. These side effects were not observed to be caused in animal experiments by the compounds according to the present invention.

3-(o-Sulfobenzoic acid imido)-piperidone-2 (the compound of Example 2 of this invention) was compared in double-blind trials with Thalidomide in leprosy patients. It was shown that its effectiveness is comparable to Thalidomide. However, as this compound has shown no teratogenic effects in animals it is, with respect to therapeutic application, superior to Thalidomide. Known 3-(o-sulfobenzoic acid imido)-piperidinedione-2,6 shows no significant effects in the treatment of leprosy.

As sedatives and hypnotics also the compounds according to the present invention display advantages compared to known substances. This was shown by controlled motility studies in mice. For these studies the established drum methods were used; the activity was monitored and determined by means of rotation recorders. The motility of mice was first pretested. Thereafter the animals received 75 mg/kg body weight of the test compounds suspended in carboxymethylcellulose. Thirty minutes after administration the motility was again determined. The difference between pre-test and test were compared with values obtained in animals which received carboxymethylcellulose alone. The difference between treated animals and controls were expressed in percentages. 3-(o-sulfobenzoic acid imido)-piperidone-2 caused a decrease of motility of 50% whereas 3-phthalimido-piperidinedione-2,6 caused a decrease of 38% and 3-(o-sulfobenzoic acid imido)-piperidinedione-2,6 caused a decrease of 31% only. Compared to other known sedatives and hypnotics no influence on coordination and blood pressure were observed under treatment with compounds of the general formula I.

The toxicity is very low. The $LD_{50}$ (standard amount which causes death of 50% of the animals investigated) in mice ranges beyond 7000 mg/kg body weight after oral administration and beyond 5000 mg/kg body weight after subcutaneous injection, for instance, of the product of example 2.

Similarly favorable effects could be observed with other compounds of the general formula I. This is illustrated in the following table which shows the results obtained in the drum test after oral administration of 200 mg compound/kg body weight.

| Compound of example No. | Motility changes in % |
|---|---|
| 2 | − 85 |
| 4 | − 70 |
| 10 | − 50 |
| 11 | − 38 |
| 12 | − 31 |
| 13 | − 54 |

Significant sedative effects were achieved with other methods also. Immediately after administration of the compounds, single male mice were put into small cages, and the movements of the cages were continuously determined by means of recorders over a period of 2 hours. The intensity and frequency of movements of the treated animals were compared with untreated controls. The results obtained by this "activity cage procedure" using 200 mg compound/kg body weight were as follows.

| Compound of example No. | Motility changes in % |
|---|---|
| 2 | −80 |
| 4 | −78 |
| 10 | −69 |
| 13 | −12 |

Favorable effects were also observed by activity measurements carried out in the dark. Immediately after administration of the compounds collectives of 10 male mice were put into dark cages equipped with 6 infra red beams. Movements caused beam interruptions. These interruptions were determined electronically over a period of 60 minutes. The movements were recorded as amplitudes. The lengths of all amplitudes obtained within 1 hour were summarized. These sums represented the total motility which was compared with those obtained in untreated controls. The differences again were expressed in percentages. The results achieved in activity measurements of mice treated orally with 200 mg/kg body weight and using this "infra red photometer procedure" are demonstrated in the next table.

| Compound of example No. | Motility changes in % |
|---|---|
| 2 | −38 |
| 4 | −54 |
| 10 | −21 |
| 11 | −16 |
| 12 | −48 |

-continued

| Compound of example No. | Motility changes in % |
| --- | --- |
| 13 | −34 |

The compounds of general formula I may be used for oral or parenteral applications. In addition they can be combined with other drugs; such other drugs can be effective as sedatives or hypnotics. However, they may also act as analgetics, spasmolytics and antipyretics. Compounds developed on the basis of formula I may be used in treatment of leprosy reactions and can be combined also with anti-infectious drugs such as diaminodiphenylsulfones or even with antibiotics.

In production of tablets, pills, dragees and similar application forms, generally used inorganic or organic adjuvants are added to the compounds of the general formula I. Such adjuvants may be for tablets and dragees: lactose, starch, talcum, octodecanoic acid, magnesium stearate and so on; for syrups, drops and the like: sugar-, invert sugar-, glucose solutions and so on; for drugs of parenteral application: water, mono-or polyhydric alcohols, vegetable fats and so on; for suppositories: natural or hydrogenated oils, waxes and so on.

Moreover suitable preservatives, stabilizers, wetting-, dissolving- and sweetening agents as well as coloring and aromatizing materials may be added. The pharmaceutical compositions of the inventions are prepared in accordance with traditionally accepted standards.

The compounds of the invention are administered in dosages effective to cause the condition desired. When the compounds are used as sedatives, a dosage of 10 to 500 mg, advisably 50 to 200 mg/patient is suitable. As sedative (for day applications) about 1 to 100 mg, advisably 20 to 50 mg/patient administered one to three times daily is suitable.

The compounds of the general formula I may be prepared by reacting a compound of the general formula

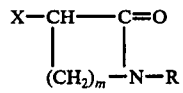

wherein R and m represent the same substituents and numerals as indicated herein above and X indicates a halogen atom, preferably a chlorine, bromine or iodine atom with a compound of the general formula

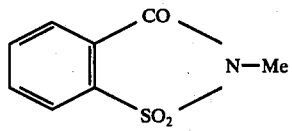

wherein Me indicates a metal, preferably sodium or potassium,

The reaction is carried out generally by dissolving a compound of the general formula II in a suitable solvent and combining it with a dissolved or suspended compound of the general formula III to form the desired compound of formula I. The course of reaction can be observed by measuring the rate of the generated MeX. Suitable reaction media are dimethylformamide, methanol, ethanol, benzene, toluene or similar solvents or diluents. Preferably the reaction is carried out at boiling temperature of the used medium but by lengthening the reaction time it may be carried out at room temperature or under cooling. For working up the reaction mixture it can be diluted with water and extracted with suitable organic solvents as ether, hydrocarbons, halogenated hydrocarbons and so on. However, the used solvent can be distilled off, too, and the remaining residue can be purified by recrystallization.

The compounds of the general formula I may also be prepared by reacting a compound of the general formula

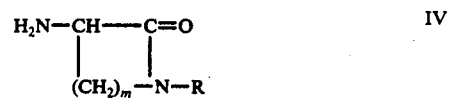

wherein R and m has the same meaning as indicated above, or a salt of a compound of the general formula IV with o-sulfobenzoic acid dichloride or -dibromide or with o-sulfobenzoic acid anhydride. Practically the reaction is performed in inert solvents, if necessary under cooling and if desired by adding an acid binding compound as triethylamine, trimethylamine, diisopropomethylamine, sodium carbonate or potassium carbonate. As solvents ether and hydrocarbons are preferred. Working up is done as described above.

Furthermore, the compounds of the general formula I may be prepared by cyclization of a compound of the general formula

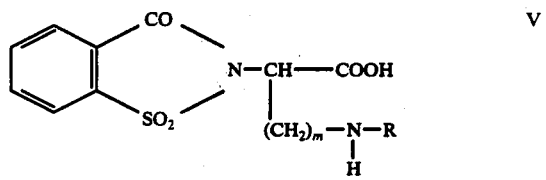

wherein R and m have the same meaning as indicated above.

The cyclization may be performed by means of phosphorous pentachloride, thionylchloride, acetylchloride, hydrogenchloride or similar compounds. However, cyclization can be also performed by elevated temperature only. If desired a functional derivative of an acid of the general formula V can be used, for example an acid halogenide, an amide or an ester.

A compound of the general formula V or a functional derivative thereof can be obtained for example by catalytically hydrogenating a alpha -(o-sulfobenzoic acid imido)- omega -cyanic acid or its ester, as described in example 6. For this it is not necessary to isolate the compound of the general formula V; the crude product obtained by hydrogenation can be used for cyclization.

The compounds of the general formula I may also be prepared by cyclization of a compound of the general formula

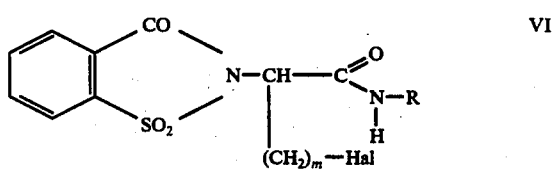

wherein R and m have the same meanings as indicated above and Hal represents a halogen atom in presence of an organic or inorganic base. As bases there can be used for example ammonia, sodium acetate, sodium carbonate, alkali alcoholates or amines. An amine can additionally be used as solvent, but other solvents as benzene, toluene or alcohols can be used, too. The reaction proceeds at room temperature as well as at elevated temperature. Working up of the reaction mixture is carried out as described in the before-mentioned processes.

Compounds of the general formula

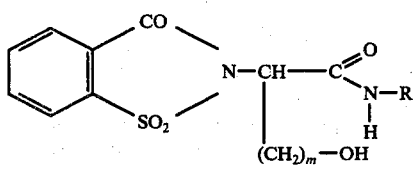

wherein R and *m* have the same meanings as indicated above can be cyclizised to compounds of the general formula I by adding acidic dehydrating agents, as for example thionylchloride, acetylchloride or acetic acid anhydride. Cyclization can be effected also by using only elevated temperature, too, such as above 60° C.

Furthermore, compounds of the general formula I, wherein R represents hydrogen, can be obtained by reacting an oxime of the general formula

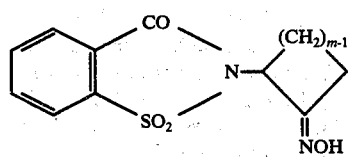

wherein *m* has the meaning indicated above, under acidic conditions, preferably by using polyphosphoric acid, sulfuric acid or glacial acetic acid according to the Beckmann's rearrangement.

The compounds of the general formula I contain one asymmetrically substituted carbon atom and, therefore, may exist in isomeric forms. Accordingly within the scope of the present invention are not only the racemic forms of the compounds of formula I, but also the pure isomers, for instance, the optically active forms of the compounds of formula I, the dextro- and the levo- form and the manufacture of these different forms.

The following not limiting examples serve further to illustrate the invention. All melting points are uncorrected.

EXAMPLE 1

15.8 g of 3-bromo-pyrrolidone-2 and 21 g of dried sodium salt of o-sulfobenzoic acid imide are refluxed in 70 ml of distilled dimethylformamide under stirring for 15 minutes. After cooling 280 ml of water are added and the mixture is extracted with chloroform. The combined chloroform extracts are dried over magnesium sulfate. The solvent is distilled off under reduced pressure and the oily residue is dissolved in ethyl acetate. On cooling 3-(o-sulfobenzoic acid imido)-pyrrolidone-2 is obtained in white crystals. The melting point is 219°–223° C after recrystallization from n-butanol. Yield 31% of theoretical.

EXAMPLE 2

63.8 g of 3-bromo-piperidone-2 and 85 g of dried sodium salt of o-sulfobenzoic acid imide are refluxed in 275 ml of distilled dimethylformamide under stirring for 15 minutes. After cooling 1.100 ml of water are added and the reaction mixture is stirred for 30 minutes. The white precipitate is filtered off, washed with water and dried under reduced pressure at 80° C. After recrystallization from n-butanol the 3-(o-sulfobenzoic acid imido)-piperidone-2 is obtained. The melting point is 246°–248° C. Yield 75% of theoretical. This compound is highly effective as a sedative.

EXAMPLE 3

26.5 g of alpha-bromo-caprolactam and 57 g of dried sodium salt of o-sulfobenzoic acid imide are refluxed in 120 ml of distilled dimethylformamide under stirring. The amount of insoluble sodium bromide can be taken as a measure for the progress of the reaction. When the precipitation of sodium bromide is finished the reaction mixture is refluxed for 10 minutes. The solvent is distilled off under reduced pressure. 150 ml of water are added to the oily residue and the mixture is stirred until crystallization sets in. The precipitate is filtered off, washed with water and dried. After recrystallization from acetic acid and from ethyleneglycol monoethylether alpha -(o-sulfobenzoic acid imido)-caprolactam has the melting point of 261°–264° C (with decomposition). Yield 52% of theoretical.

EXAMPLE 4

23.9 g of o-sulfobenzoic acid dichloride, melting point 79° C (Beilstein 11, 374) are dissolved in 160 ml of absolute ether. On cooling 12.8 g of 1-methyl-3-aminopiperidone-2 are added followed by the dropwise addition of 28 ml of triethylamine during four hours. The reaction temperature is maintained within 0°–5° C for some more hours. Thereafter the mixture is maintained at room-temperature for some time and then refluxed for some more hours. After cooling to 0° C the precipitate is filtered off and washed with water. The ether-filtrate is concentrated under reduced pressure to dryness. The precipitate and the residue of the ether solution are combined and recrystallized from n-butanol. Thus, 1-methyl-3-(o-sulfobenzoic acid imido)-piperidone-2 is obtained in white crystals; melting point 160°–162° C. Yield 54% of theoretical. This is an especially effective sedative.

EXAMPLE 5

21.2 g of 1-methyl-3-bromo-piperidone-2 are dissolved in 85 ml of absolute dimethylformamide. 26.2 g of dried sodium salt of o-sulfobenzoic acid imide are added and the reaction mixture is refluxed for 15 minutes. After cooling the solution is added to 440 ml of water. The precipitate thus obtained is filtered off, dried over phosphorous pentoxide at 80° C under reduced pressure and recrystallized from n-butanol. The melting point of 1-methyl-3-(o-sulfobenzoic acid imido)-piperidone-2 is 160°–162° C. The compound is identical with that obtained in example 4. Yield 51% of theoretical.

The starting material 1-methyl-3-bromo-piperdone-2 is obtained in the following manner:

28.5 of 1-methyl-piperidone-2 are dissolved in 252 ml of chloroform and cooled to 0° C. 105 g of phosphorus pentachloride and 1.2 g of zinc chloride are added. The mixture is warmed to 20 C and 26 ml of bromine are added dropwise during 1.5 hours. The reaction mixture is heated to 45° C for 5 hours.

The precipitate is filtered off and suspended in 250 ml of ice-water. The filtrate is evaporated to dryness and the residue is suspended in ice-water too. The aqueous solutions are combined and extracted with chloroform several times. The combined chloroform extracts are decolored with a solution of sodium hydrosulfite. After drying the solvent is distilled off. On adding ether the residue crystallized. The 1-methyl-3,3-dibromo-piperidone-2 is obtained; melting point 69°–73° C.

36.0 g of said compound and 11.9 g of anhydrous sodium acetate are dissolved in 325 ml of acetic acid. 5 g of palladium-charcoal catalyst (5%Pd) are added and the mixture is hydrogenated under normal pressure until ca. 3,630 ml of hydrogen are absorbed. The catalyst is filtered and the solvent is distilled off under reduced pressure. The residue is dissolved in 350 ml of water, neutralized with sodium bicarbonate and extracted with chloroform for several times. The combined chloroform-extracts are dried with magnesium sulfate and the solvent is distilled off under reduced pressure. The oily residue consists of 1-methyl-3-bromo-piperdone-2 and can be used for the following reaction without further purifications.

EXAMPLE 6

16.5 g of alpha -(o-sulfobenzoic acid imido)-gamma-cyano-butyric acid ethylate are dissolved in 150 ml of dioxane. 5 g of Raney-nickel are added and the mixture is hydrogenated in an autoclave at about 1500 pound/square inch hydrogen pressure and 70°–100° C for 1.5 hours. After cooling and filtration the filter cake is decomposed with 2 n-hydrochloric acid. The residue thus obtained consists of 3-(o-sulfobenzoic acid imido)-piperidone-2, identical with the compound obtained in example 2. The melting point is 246°–248° C after recrystallisation from n-butanol.

From the dioxane-solution another part of the described compound is obtained by distilling off the solvent. The overall yield is 62% of the theoretical one.

On using platinum oxide as catalyst and glacial acetic acid as solvent an identical compound is obtained.

The above mentioned starting material alpha-(o-sulfobenzoic acid imido)-gamma-cyano-butyric acid ethylate is obtained in the following manner:

51.5 g of alpha-bromo-gamma-cyano-butyric acid ethylate are dissolved in 150 ml of absolute dimethylformamide and 51.5 g of dried sodium salt of o-sulfobenzoic acid imide are added. Under stirring the reaction mixture is heated to 110° C for 45 minutes. After cooling the mixture is diluted with 600 ml of water and extracted with ether for several times. The combined ether extracts are dried with magnesium sulfate and filtered. The solvent is distilled off under reduced pressure. The oily residue is dissolved in 120 ml of absolute ethanol. On chilling alpha-(o-sulfobenzoic acid imido)-gamma-cyano-butyric acid ethylate is obtained. Melting point: 67°–71° C.

EXAMPLE 7

37.5 g of alpha-(o-sulfobenzoic acid imido)-delta-bromo-pentanoic acid monomethylamide are dissolved in 400 ml of xylene. 14.2 g of ethyl-diisopropylamine are added and the mixture is refluxed for two hours. On cooling, if necessary after concentrating, 1-methyl-3-(o-sulfobenzoic acid imido)-piperidone-2 precipitates. Upon recrystallization from n-butanol, the product is obtained which has a melting point of 160°–162° C, identical with that of example 4. The yield is 71% of theoretical.

EXAMPLE 8

28.4 g of alpha-(o-sulfobenzoic acid imido)-gama-hydroxy-butyric acid amide are dissolved in 250 ml of xylene and refluxed for some hours, using a water separator. When the theoretical amount of water is obtained, the reaction mixture is cooled. 3-(o-sulfobenzoic acid imido)-pyrrolidone-2 precipitates, sometimes after concentrating the solution. The compound is identical with that of example 1. Melting point: 219°–223° C.

EXAMPLE 9

10 g of the oxime of 2-(o-sulfobenzoic acid imido)-cyclopentanone are dissolved in 300 ml of polyphosphoric acid and heated to 125° C for 20 minutes. After cooling the reaction mixture is diluted with 1000 ml of water and extracted with chloroform for several times. The combined chloroform extracts are dried and the solvent is distilled off. The oily residue is recrystallized from n-butanol. The melting point is 246°–248° C. The compound is identical with that of example 2. The starting material is obtained in the following manner:

36 g of 2-chloro-cyclopentanone are dissolved in 400 ml of absolute dimethylformamide. 54 g of dried sodium salt of o-sulfobenzoic acid imide are added and the reaction mixture is heated to 130°–140° C for 2 hours. The precipitated sodium chloride is filtered off and the solution is concentrated under reduced pressure. The residue is dissolved in water and extracted with ether. The ether is distilled off and the residue is dissolved in acetone. On adding ligroin (boiling 90°–120° C) a white precipitate is obtained. It is recrystallized from ethylacetate, melting point 163°–165° C.

27 g of said compound are dissolved in 500 ml of ethanol, 7 g of hydroxylamine hydrochloride, dissolved in 250 ml of water, and 5 g of sodium carbonate are added. The reaction mixture is refluxed for 30 minutes. On cooling the oxime, melting point 175°–180° C, is obtained.

EXAMPLE 10

9 g of 1-ethyl-3-bromo-piperidone-2 are dissolved in 34 ml of absolute dimethylformamide. 10.4 g of dried sodium salt of o-sulfobenzoic acid imide are added and the mixture is refluxed for 15 minutes. After cooling to room temperature the reaction mixture is added to 175 ml of water. On stirring, if necessary after adding some ether, the precipitated oil crystallized. The precipitate is filtered, washed with water and dried under reduced pressure at 60° C. After recrystallization from n-butanol there is obtained 1-ethyl-3-(o-sulfobenzoic acid imido)-piperidone-2. It has the melting point 147°–150° C. Yield 42% of theoretical.

The starting material 1-ethyl-3-bromo-piperidone-2 is obtained on following the procedure described in example 5. The intermediate 1-ethyl-3,3-dibromo-piperidone-2 has the melting point 33°–35° C.

EXAMPLE 11

19.2 g of 1-propyl-3-bromo-piperidone-2 are dissolved in 68 ml of absolute dimethylformamide. This solution is added to 20.8 g of dried sodium salt of o-sulfobenzoic acid imide and the mixture is refluxed for 10 minutes under stirring. After cooling to room temperature the mixture is added to 350 ml of water and extracted with chloroform. The extracts are dried over magnesium sulfate and the solvent is distilled off under reduced pressure. The residue crystallizes by adding 100 ml of ether. The precipitated 1-propyl3-(o-sulfobenzoic acid imido)-piperidone-2 is recrystallized from n-butanol. The melting point is 129°–131° C. Yield 36% of theoretical.

The starting material 1-propyl-3-bromo-piperidone-2 is obtained on following the procedure described in example 5. The intermediate 1-propyl-3,3-dibromo-piperidone-2 does not crystallize.

EXAMPLE 12

On following the procedure described in example 11 1-isopropyl-3-(o-sulfobenzoic acid imido)-piperidone-2 is obtained from 1-isopropyl-3-bromo-piperdone-2. The melting point is 166°–168° C after recrystallization from n-butanol. Yield 38% of theoretical.

The starting material 1-isopropyl-3-bromo-piperidone-2 is obtained on following the procedure described in example 5. The intermediate 1-isopropyl-3,3-dibromo-piperidone-2 crystallizes on adding ligroine. The melting point is 73°–75° C. The mono-bromo compounds used in examples 10–13 as starting materials are used as crude oils without further purification.

EXAMPLE 13

10 g of 1-methyl-3-bromo-pyrrolidone-2 are dissolved in 44 ml of absolute dimethylformamide. 13.4 g of dried sodium salt of o-sulfobenzoic acid imide are added and the reaction mixture is refluxed for 10 minutes under stirring. After cooling to room temperature the reaction mixture is added to 230 ml of water. It is extracted with chloroform for several times, the extracts are combined and dried over magnesium sulfate. The solvent is distilled off under reduced pressure and the residue is dissolved in 50 ml of hot n-butanol. After cooling 100 ml of ether are added. The precipated crystals are filtered and recrystallized from n-butanol. The 1-methyl-3-(o-sulfobenzoic acid imido)-pyrrolidone-2 thus obtained, has the melting point 141°–143° C. Yield 32% of theoretical.

The starting material 1-methyl-3-bromo-pyrrolidone-2 is obtained on following the procedure described in example 5. The intermediate 1-methyl-3,3-dibromo-pyrrolidone-2 has the melting point of 64°–73° C.

Typical pharmaceutical compositions of the invention can be prepared as follows:

EXAMPLE A 100.0 g of 3-(o-sulfobenzoic acid imido)-piperidone-2 obtained according to example 2, 55.0 g of microcrystalline cellulose, 100.0 g of anhydrous lactose and 5.0 g of magnesiums stearate are sieved and intimately mixed. Said mixture is tabletted to tablets of 260.0 mg. each, and a diameter of 9 mm. Each tablet contains 100 mg of the active agent.

EXAMPLE B 100.0 g of 3-(sulfobenzoic acid imido)-piperidone-2, 60.0 g of dicalcium phosphate and 30.0 g of corn starch are passed through a sieve no. V (German Pharmacopeia 7) and intimately mixed. (Mixture 1). 10.0 g of polyvinylpyrrolidone are dissolved in water. The mixture 1 is humidified with the aqueous polyvinylpyrrolidone solution, the moist granulate is passed through a 2 mm sieve, dried at 40° C to an amount of moisture of 2%, and passed through a 1 mm sieve. The resulting granulate is mixed with 30.0 g of corn starch, 7.0 g of talc and 3.0 g of magnesium stearate. Said mixture is tabletted to tablets of 240,0 mg each, serving as dragee cores.

These cores are sugar-coated in the conventional manner giving dragees with a weight of about 400 mg. Each dragee contains 100 mg of the active agent.

EXAMPLE C 462.5 g of cocoa butter or the same amount of a synthetic suppository base are melted and triturated with 37.5 g of 3-(o-sulfobenzoic acid imido)-piperidone-2. The mixture is poured into suppository molds each containing 2 g of the mixture, and the mold is cooled to solidify the suppositories. Each suppository contains 150 mg of the active compound.

EXAMPLE D

Capsules, each containing 75 mg of 3-(o-sulfo-benzoic acid imido)-piperidone-2 are prepared by intimately mixing 75 g of said compound with 38.5 of dicalcium phosphate, 1.25 g of liquid paraffin (German Pharmacopeia 7) and 0.25 g of magnesium stearate, sieving said mixture and filling 115 mg thereof into each gelatine capsule.

EXAMPLE E 10 kg of tragacanth and 2 kg of sodium sorbate are humidified with distilled water. The mixture is allowed to stand for 24 hours. 400 kg of saccharose, 1.125 kg of methylparabene and 0.375 kg of propylparabene (each German pharmacopeia 7) are dissolved with water and added to the tragacanth-mixture. 20 kg of 3-(sulfo-benzoic acid imido)-piperidone-2 are sieved into the beforementioned saccharose solution and the mixture is intimately homogenized. 1.5 kg of aromatizing agents are added and the mixture is made up to 1000 l with water. 5 ml of the resulting syrup contain 100 mg of the active compound.

Clinical data of a typical compound of the invention has established the following. The sleeping behavior of 12 healthy patients was studied during 3 successive nights in a fully climatized and noise-isolated sleep-laboratory. During the first night the subjects remained untreated in order to familiarize them with their surroundings. During the second night each patient received a placebo, whereas during the third night they received 100 mg of 3-(o-sulfobenzoic acid imido)-piperidone-2, each.

The following statistically significant differences between the treatment- and the placebo-nights were found.

1. The deep-sleep phase III increased during treatment with the substance of the invention by 34%.
2. The waking phase 0 significantly decreased during the treatment night.

The REM-phase (rapid eyes movement) did not decrease under treatment, but showed a slight mean-increase from 18.4 to 20.1%, a difference which is not significant statistically.

There were no side effects apparent during the treatment with 3-(o-sulfobenzoic acid imido)-piperidone-2. Blood status, enzymatic reactions as well as plasma lipid and cholesterol levels remained unchanged.

Preferred and of high effectiveness as sedatives are the piperidones especially the beforementioned 3-(o-sulfobenzoic acid imido)-piperidone-2.

We claim:

1. A pharmaceutical composition having therapeutic properties as sedative and hypnotics comprising a compound of the general formula

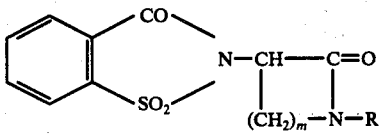

wherein R is a hydrogen atom or an alkyl radical with 1 to 3 carbon atoms and $m$ is 2, 3 or 4, in a therapeutically effective amount to induce sedation, and a pharmaceutically acceptable carrier.

2. The composition of claim 1 wherein in the formula R is hydrogen.

3. The composition of claim 1 wherein in the formula $m$ is 2.

4. The composition of claim 1 wherein in the formula $m$ is 3.

5. The composition of claim 1 wherein in the formula $m$ is 4.

6. The composition of claim 1 wherein in the formula R is alkyl of 1 to 3.

7. The composition of claim 6 wherein in the formula $m$ is 3.

8. The composition of claim 1 wherein the compound is selected from the group consisting of 3-(o-sulfobenzoic acid imido)-pyrrolidone-2, 3-(o-sulfobenzoic acid imido)-piperidone-2, alpha-(o-sulfobenzoic acid imido)-caprolactam, 1-methyl-3-(o-sulfobenzoic acid imido)-piperidone-2, 1-ethyl-3-(o-sulfobenzoic acid imido)-piperidone-2, 1-n-propyl-3-(o-sulfobenzoic acid imido)-piperidone-2, 1-i-propyl-3-(o-sulfobenzoic acid imido)-piperidone-2, and 1-methyl-3-(o-sulfobenzoic acid imido)-pyrrolidone-2.

9. The pharmaceutical composition of claim 1 wherein the compound is present in a therapeutically effective amount of from about 1 to about 500 mg/kg body weight.

10. The pharmaceutical composition of claim 9 wherein the therapeutically effective amount is from about 50 to about 200 mg/kg body weight.

11. The pharmaceutical composition of claim 9 wherein the therapeutically effective amount for daily application is from about 1 to about 100 mg/kg body weight administered one to three times daily.

12. The pharmaceutical composition of claim 11 wherein the therapeutically effective amount is from about 20 to about 50 mg/kg body weight administered one to three times daily.

13. The pharmaceutical composition of claim 8 wherein the compound is 3-(o-sulfobenzoic acid imido)-piperidone-2.

14. The pharmaceutical composition of claim 13 wherein 3-(o-sulfobenzoic acid imido)-piperidone-2 is present in a therapeutically effective amount of from about 1 to about 500 mg/kg body weight.

15. The pharmaceutical composition of claim 1 in suitable form of oral administration.

16. The method of inducing sedation in warm-blooded animals which comprises administering to said warm-blooded animals a pharmaceutical composition comprising a compound of the general formula

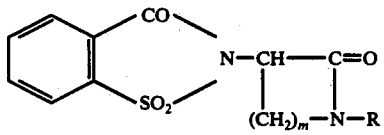

wherein R is a hydrogen atom or an alkyl radical with 1 to 3 carbon atoms and $m$ is 2, 3 or 4 in a controlled dosage effective to induce sedation.

17. The method of claim 16 wherein R is hydrogen.

18. The method of claim 16 wherein $m$ is 2 to 4.

19. The method of claim 16 wherein R is alkyl of 1 to 3.

20. The method of claim 19 wherein $m$ is 3.

21. The method of claim 16 wherein the compound is selected from the group consisting of 3-(o-sulfobenzoic acid imido)-pyrrolidone-2, 3-(sulfobenzoic acid imido)-piperidone-2, alpha-(o-sulfobenzoic acid imido)-caprolactam, 1-methyl-3-(o-sulfobenzoic acid imido)-piperidone-2, 1-ethyl-3-(o-sulfobenzoic acid imido)-piperidone-2, 1-n-propyl-3-(o-sulfobenzoic acid imido)-piperidone-2, 1-i-propyl-3-(o-sulfobenzoic acid imido)-pyrrolidone-2 and 1-methyl-3-(o-sulfobenzoic acid imido)-pyrrolidone-2.

22. The method of claim 16 wherein the controlled dosage effective to induce sedation is from about 1 to 500 mg/kg body weight.

23. The method of claim 22 wherein the controlled dosage effective to induce sedation is from about 50 to 200 mg/kg body weight.

24. The method of claim 16 wherein the controlled dosage effective to induce sedation for daily application is from about 1 to 100 mg/kg body weight administered one to three times daily.

25. The method of claim 24 wherein the controlled dosage to induce sedation of daily application is from about 20 to 50 mg/kg body weight administered one to three times daily.

26. The method of claim 21 wherein the compound is 3-(o-sulfobenzoic acid imido)-piperidone-2.

27. The method of claim 26 wherein the controlled dosage effective to induce sedation is from about 1 to 500 mg/kg body weight.

28. The method of claim 16 in which the compound is administered orally.

* * * * *